United States Patent [19]

Stanisiewski

[11] Patent Number: 5,583,106
[45] Date of Patent: Dec. 10, 1996

[54] SOMATOTROPIN FOR INCREASING REPRODUCTIVE PERFORMANCE IN CATTLE

[75] Inventor: Edward P. Stanisiewski, Richland, Mich.

[73] Assignee: The Upjohn Company, Kalamazoo, Mich.

[21] Appl. No.: 193,369

[22] Filed: Feb. 8, 1994

Related U.S. Application Data

[63] Continuation of Ser. No. 746,668, filed as PCT/US92/06384 Aug. 6, 1992, abandoned.

[51] Int. Cl.$^6$ .................................................. A61K 38/27
[52] U.S. Cl. ............................. 514/12; 514/21; 530/399
[58] Field of Search ........................ 514/12, 21; 530/399

[56] References Cited

U.S. PATENT DOCUMENTS

| | | | |
|---|---|---|---|
| 5,004,728 | 4/1991 | Chalupa et al. | 514/12 |
| 5,008,244 | 4/1991 | Miller et al. | 514/12 |

OTHER PUBLICATIONS

A. L. Richard, et al., "Responses of Dairy Cows to Exogenous Bovine Growth Hormone Administered During Early Lactation", Journal of Dairy Science, vol. 68, No. 9, pp. 2385–2389 (1985).

F. Elvinger, et al., "Effects of Administration of Bovine Somatotropin on Milk Yield and Composition", Journal of Dairy Science, vol. 71, No. 6, pp. 1515–1525 (1988).

E. P. Stanisiewski, et al., "Milk Yield, Health, and Reproduction of Dairy Cows Given Somatotropin (Somavubove) Beginning Early Postpartum", vol; 75, No. 8, pp. 2149–2164 (1992).

Holcombe et al., Anim. Prod., vol. 46, pp. 195–202, 1988.

Cole et al., J. Dairy Sci., vol. 75, pp. 111–123, 1992.

Lapierre et al., Can. J. Anim. Sci, vol. 68, pp. 741–749, 1988.

Lormore et al., J. Dairy Sci, vol. 73, pp. 3237–3247, 1990.

Chalripa et al J. Dairy Sci, vol. 72:2510–2524 (1989).

*Primary Examiner*—Chhaya D. Sayala
*Attorney, Agent, or Firm*—James D. Darnley, Jr.; Gregory W. Steele

[57] ABSTRACT

This invention provides a method of using somatotropin to enhance the reproductive performance in cattle by commencing administration during the early postpartum period. Following one aspect of the invention, somatotropin (5 mg/day) is administered starting at five days postpartum, continuing until the animal becomes pregnant or until about 100 days postpartum.

14 Claims, No Drawings

SOMATOTROPIN FOR INCREASING REPRODUCTIVE PERFORMANCE IN CATTLE

CROSS REFERENCE TO RELATED APPLICATIONS

The present application is a continuation of International Application Ser. No. PCT/US92/06384, filed 6 Aug. 1992, which is a continuation of U.S. Ser. No. 07/746,668, filed 16 Aug. 1991, now abandoned.

FIELD OF THE INVENTION

This invention relates to a method of using somatotropin to increase the reproductive performance of cattle and particularly, administration of somatotropin beginning during the early postpartum period to increase reproductive performance of cattle.

BACKGROUND OF THE INVENTION

The underlying concept behind a dairy operation is that cows must become pregnant, carry a calf to term, and with parturition begin producing milk. Not only is pregnancy a prerequisite for milk production in the dairy herd, but female offspring become the future producers in both the beef and dairy herd. Using current production capabilities with average herd cows, it is believed in the dairy industry that lifetime production of cattle is maximized when calving intervals are maintained at approximately twelve month, approximately 360 day, intervals. Using this 360 day interval, parturition is considered day zero (0). Following parturition, the animal requires a period of time to return to estrus. In dairy cows this can occur as early as the first 14 days, but more frequently occurs later, e.g., 30 to 72 days. Since gestation lengths of cattle are fixed at about 280 days, cows must become pregnant again within about 150 days postpartum so that a reasonable calving interval can be maintained while at the same time maximizing production. The cow being on an approximately 21 day estrus cycle, a delay in the return to estrus, or failure to conceive with insemination following return to estrus, can cause disruption of the 360 day interlactation interval. However, the early postpartum interval represents a period when milk yields are maximum, and appetite (feed intake) is usually inadequate to meet production needs. Cattle must therefore mobilize their own body stores of fat to support milk production. When tiffs mobilization occurs, cattle are said to be in a state of negative energy balance. Negative energy balance is considered to be detrimental to reproductive efficiency in cattle. See, e.g., Butler, et al., J. Animal Science, 53:742 (1981). Thus, it is one goal of the herd manager to maximize milk production while at the same time minimizing the deleterious effect of somatotropin on energy balance.

Bovine somatotropin is produced in the anterior pituitary gland and the metabolic effects of this 190 to 191 amino acid protein are varied. For instance, it has been known for years that this substance causes an increase in milk production. However, this is not the only effect of somatotropin as other metabolic changes, including glucose and lipid metabolism, skeletal growth, and protein synthesis, have been reported. In addition, since high milk production causes the cow to enter negative energy balance, numerous studies have been conducted on the effect of somatotropin on both milk production and reproductive performance. Most of these studies report that somatotropin treatment has no significant effect on reproductive performance; some, using somatotropin at relatively high concentrations or early in the postpartum period, have reported some reduction in reproductive efficiency. These studies which report a negative effect on reproduction have used what can be called a therapeutic dose of somatotropin, i.e. the amount of somatotropin necessary to enhance milk production, which is generally recognized to be about 5 to 50 mg/animal/day.

According to the method of the present invention, it has been found that cattle administered somatotropin starting in the early postpartum period show improved reproductive efficiency compared with herdmates. The dose of somatotropin which is effective at improving reproductive performance is the equivalent of less than 14 mg of somatotropin per cow per day. Treatment at this dose of somatotropin continues until the animal is once again pregnant or until about 100 days postpartum, whichever occurs first. Following cessation of treatment during this first period, treatment with somatotropin continues at a maximally efficacious dose to maintain high milk yields which are typical of animals undergoing somatotropin treatment. Surprisingly, treatment of dairy cattle with somatotropin following the method of the invention also results in an increase in FCM (fat corrected milk) which is greater than that which is seen when only higher doses of somatotropin are used.

INFORMATION DISCLOSURE

PCT Application WO 90/14100, publication date 29 Nov. 1990, discloses a method of increasing fertility in food producing animals by administrating somatotropin during the period of growth (the finishing stage) just prior to the reproductive or market stage of growth. The present invention does not require administration during the finishing stage of growth.

Z. Ibrahim, et at., "The Use of Biosynthetic Human Growth Hormone to Augment Ovulation Induction with Buserelin Acetate/Human Memopausal Gonadotropin in Women with a Poor Ovarian Response", Fertility and Sterility, vol. 55, No. 1, (January 1991), report that human growth hormone stimulates the rate of growth of follicles in women also being treated with buserelin acetate and human menopausal gonadotropin. The present invention requires no such additional treatment.

R. Hornburg, et al., "Growth Hormone Facilitates Ovulation Induction by Gonadotrophins", Clinical Endocrinology, vol. 29, pp. 113–117 (1988), report that human growth hormone stimulates ovarian response to gonadotropin in women previously shown to be resistant to gonadotropin treatment. The present invention, however, is useful in the postpartum period.

There are numerous studies which have examined the effect of bSt administration on animal reproduction. For example:

M. Lucy, "Effects of Calcium Salts of Long-Chain Fatty Acids, Growth Factors, and Energy Balance on Ovarian Follicular Dynamics in Postpartum Dairy Cows" (Doctoral Dissertation, University of Florida, 1990), reports a study wherein lactating cattle are treated with 25 mg/d of bovine somatotropin (bSt) commencing between 60 and 100 days postpartum. It is reported that bSt treatment causes an increase in the mid-size follicles but not in the large follicles.

D. E. Bauman, et al., "Responses of High-Producing Dairy Cows to Long-Term Treatment with Pituitary Somatotropin and Recombinant Somatotropin, Production Research Paper", J Dairy Science, 68:1352–1362 (1985), report that the reproductive parameters of bSt treated heifers are the same or better than resident herd averages. Unlike the protocol disclosed here, however, administration of bSt commences at approximately 84 days postpartum and continued to day 188 at a minimum dose of 13.5 mg/day.

D. E. Bauman, et al., "Feeding and Management 11", J. Dairy Science, Vol. 71, p. 205 (1988), R. C. Lamb, et al, J. Dairy Science, Vol. 71, p. 208 (1988), and A. N. Pell, et al, J. Dairy Science, Vol. 71, p. 206 (1988), each report that sustained release formulations of sometribove USAN (recombinant methionyl bovine somatotropin) administered commencing at 60 days postpartum, have no effect on reproductive performance in dairy cows.

D. L. Hard, et al., J. Dairy Science, Vol. 71, p. 210 (1988), report that pregnancy and successful calving rates are lower in Holstein cows treated with a sustained release formulation of sometribove USAN commencing at day 60 postpartum.

W. A. Chalupa, et al., J. Dairy Science, Vol. 71, p. 210 (1988), report that administration of recombinant bSt at doses as low as 10.3 mg/day have no effect on days open or on pregnancy rates.

A. A. Aguilar, et al., J. Dairy Science, Vol. 71, p. 208 (1988), report that the administration of sometribove USAN have no effect on reproductive performance in dairy cows.

D. L. Palmquist, J. Dairy Science, Vol. 71, p. 206 (1988), reports no effect on reproductive performance in cows treated with as low as 10 mg/day recombinant bSt commencing at 30 days postpartum.

C. Thomas, et al., J. Dairy Science, Vol. 70, p. 175 (1987), report that recombinant bSt at doses as low as 12.5 mg/day does not influence the proportion of cows initially conceiving.

R. Rajamahendran, et al., "Effect of Single Lactation Treatment with Recombinant Bovine Growth Hormone on Reproductive Performance in Dairy Cows, Animal Reproduction Science", 24:211–216 (1991), report that daily recombinant bSt administration at 10.3 and 20.6 mg/day have no effect on reproduction in dairy cows.

The present invention differs from the above references in the timing and/or the dosage of the somatotropin administered.

SUMMARY OF THE INVENTION

In one aspect, this invention provides a method for increasing fertility in cattle, comprising administering an effective amount of somatotropin to the animal during the early postpartum period.

More specifically, this aspect of the invention comprises administering less than 14 mg/day of somatotropin to the animal commencing no sooner than 5 days postpartum.

Most particularly, this invention provides a method for increasing fertility in cattle, comprising parenteral injection of 5 mg/day of somatotropin commencing at 14 days postpartum and continuing until either pregnancy is established or until about 100 days postpartum, whichever occurs first.

A second aspect of the invention provides a method of enhancing both reproductive efficiency and fat corrected milk yield in cows which comprises:

(a) administering an effective mount of somatotropin to the cow during a first treatment period, the first treatment period beginning at day zero (0) and continuing until either pregnancy is established or until about 100 days postpartum, whichever occurs first, and (b) administering an amount of somatotropin to the cow said amount effective to cause or maintain an increase in fat corrected milk during a second treatment period, the second treatment period to commence following cessation of the first treatment period.

More particularly, this aspect of the invention comprises administration of somatotropin during the first treatment period wherein the effective amount is less than 14 mg/day and during the second treatment period wherein the effective amount is about 5 to 50 mg/day.

Most particularly, this aspect of the invention comprises administration of somatotropin wherein administration during the first treatment period commences at about day 14 of the first treatment period in an amount of 5 mg/day, and administration during the second treatment period commences one day following cessation of the first treatment period in an amount of about 14 mg/day.

A third aspect of this invention provides a method for increasing the yield of fat corrected milk in an animal, comprising administering an effective amount of somatotropin to the animal during the early postpartum period.

More specifically, this method comprises administering less than 14 mg/day of somatotropin to the animal commencing no sooner than 5 days postpartum.

Most particularly, this method comprises administration of 5 mg/day of somatotropin via subcutaneous injection, the administration to commence at 14 days postpartum and continue until about 60 days postpartum.

DETAILED DESCRIPTION

Bovine somatotropin (bSt) from any source may be used in the method of the invention, the only requirement being that the somatotropin is capable of causing the desired effect. This of course would include non-native forms of bovine somatotropin, for instance, somatotropin produced by genetically engineered organisms. Many of the somatotropin produced by recombinant means have amino acid sequences which do not conform to the native (bovine) protein but remain bioactivc, i.e. produce the desired hormonal effect. Other forms of somatotropin include those which may be administered in a form requiring activation or alteration by processes within the animal's body before the desired effect may be achieved. Somatotropin is produced in the anterior lobe of the bovine pituitary gland, and rims this tissue serves as an excellent source of bSt. Bovine somatotropin may be isolated and purified from this gland following the procedure described in C. H. Li, *J. Biol. Chem.* 211:555 (1954). Other procedures are also known in the an which arc equally suitable, see e.g. W. L. Miller, et al, *J. Biol. Chem.* 255:7521–24 (1980) and U.S. Pat. No. 4,371,462. In addition, a primary commercial source or the pituitary-derived product is A. F. Parlow, Harbor-UCLA Medical Center, Torrence Calif.

Since a bovine pituitary gland contains only about 5 to 15 mg somatotropin, see Peel and Barman, J. Dairy Science, 70:474 (1987), the use of microorganisms which have been genetically engineered to express bovine somatotropin represent an alternative and plentiful source of the somatotropin needed to practice the invention. Many such organisms have been described, see e.g. Seelbury, et al., DNA 2:37 (1983). In addition, there arc strains of *Escherichia coli* that produce bovine somatotropin which are available from the American Type Culture Collection (17th Edition, 1989) under accession numbers 39173, 39174, and 39175.

To practice the method of the invention, the person managing the cattle or dairy herd is in need of a dosage form suitable for use in the particular conditions and circumstances under which the herd is managed. The selection of any one form from those which may be available is within the skill of a person trained in the art of managing such an operation. Of course, these forms must be suitable to withstand the conditions of temperature, storage, and handling which are common to such an operation. There are many such dosage forms known to the manufacturing pharmaceutical chemist which are suitable for use under management conditions. Therefore, the somatotropin may be formulated for administration by following any number of techniques known in the art of hormone delivery, or from known formulations which are readily adapted for use in hormone delivery.

In its simplest form the somatotropin is obtained in the form of a powder and is mixed with water. Such a solution could also contain appropriate buffers, salts, preservatives, etc. Alternatively, a suspension may be employed by rendering the somatotropin insoluble by complexation, adsorption, chemical modification, or covalent bonding to other molecules.

Sustained release formulations are also suitable for administrating somatotropin for the method of this invention. These formulations generally comprise a somatotropin having decreased solubility in order to delay absorption into the bloodstream. In addition, these formulations may include other components, agents, carriers, etc. which may also serve to delay absorption of the somatotropin. Microencapsulation, polymeric entrapment systems, and osmotic pumps, which may or may not be bioerodible, may also be used to allow delayed or controlled diffusion of the somatotropin from the capsule or matrix.

The formulation may of course be administered by a number of means keeping in mind that all formulations are not suitable for every route of administration. For instance, somatotropin is not readily absorbed from the gastrointestinal tract, thus, generally, oral ingestion is not a suitable means of administration. Solutions and suspensions, assuming a suitable viscosity for ease of use, are generally injected. Suspensions too viscous for injection may be implanted using devices designed for such purposes, if necessary. Sustained release forms are generally administered via parenteral or enteric means.

Parenteral administration is the preferred route of administration of the somatotropin used to practice the invention. "Parenteral" includes formulations suitable for injection and for oral, nasal, vaginal, rectal, and buccal administration. Injection, either subcutaneous or intramuscular, is preferred; intramuscular injection is most preferred.

Any additional components of the formulation should be non-immunogenic and biocompatible, as well as capable of bioabsorption, biodegradation, or elimination as an intact molecule. The formulation may be supplied in a ready-to-use form or may be supplied as a sterile powder or liquid requiring vehicle addition prior to administration. If sterility is desired, the formulation may be made under sterile conditions, the individual components of the mixture may be sterile, or the formulation may be sterile filtered prior to use.

The administration of somatotropin according to this invention may be started at any time during the early postpartum period. However, to allow the animal to recover from parturition, it is recommended that treatment should be delayed until about 5 days postpartum. A delay of ten days is more preferable, and 14 days is preferred. The amount of somatotropin useful to enhance pregnancy during this treatment period is less than about 14 mg/day; 5 mg/day is preferred. Treatment continues until pregnancy is established or until at least about 100 days postpartum, whichever is first to occur.

It is generally recognized by those skilled in the art of dairy herd management that treatment with bovine somatotropin for the purpose of increasing milk yields should commence at about 75 to 100 days postpartum. Typically, the amount of somatotropin administered as compared to non-treated herdmates, is in the range of 25 to 50 mg/day. Thus, following cessation of treatment during the early postpartum period according to one aspect of the invention, a second aspect of the invention provides that administration of somatotropin continue at the maximally efficacious dose to maintain high milk yields, e.g. about 5 to 50 mg/day. Fourteen mg/day is preferred.

These terms, as used throughout the specification and claims, are defined as follows:

"D" means day.

"Reproductive performance" and "reproductive efficiency" include the following parameters: days open, conception rate, first service conception rate, second service conception rate, pregnancy rate, and services per conception.

"Days open" means the number of days from last calving to date of breeding in association with continued pregnancy.

"Conception rate" means the number of cows pregnant per number bred.

"First service conception rate" means the number of cows pregnant to first artificial insemination (AI) per number bred first time post calving.

"Second service conception rate" means the number of cows pregnant to second AI per number bred second time post calving.

"Pregnancy rate" means the number of cows pregnant per total number available within a treatment group.

"Services per conception" means the number of services (AI) per total number pregnant.

"Cattle" includes cows reared for both beef and dairy purposes.

"Postpartum" is that period of time of the reproductive cycle in cow which begins at calving (day zero (0)) and continuing throughout lactation (about 305 days). "Early postpartum" is that portion of the postpartum period from day zero (0) through about sixty (60) days.

"Somatotropin" or "St" as used here refers to bovine somatotropin derived from any source and includes St isolated from, or produced by, bovine pituitary gland and/or recombinant organisms.

The following serves to exemplify the invention and in no way should be construed as limiting the scope of the invention.

Animals and Treatments: Two hundred ten lactating multiparous Holstein cows located at a commercial dairy in Southwest Michigan are utilized for this study. As cows calved, they are blocked between 11 and 14 d postpartum into replicates of 5. Cows within each block are randomly assigned to 1 of 5 treatments prior to 14 d postpartum. The treatment groups consisted of: non-injected controls through d 130 postpartum (C), non-injected through d 60 postpartum, then injected intramuscularly (IM) with 14 mg rbSt daily from d 61 through d 130 postpartum, i.e. zero to high dosing (OH), injected IM with 5 mg rbSt daily from d 14 through d 130 postpartum, i.e. low dosing (L), injected IM with 5 mg rbSt daily from d 14 through d 60 postpartum, then injected IM with 14 mg rbSt daily from d 61 through d 130 postpartum, i.e. low to high dosing (LH), injected IM with 14 mg rbSt daily from d 14 through d 130 postpartum, i.e. high dosing (H).

Injections of rbSt begin on d 14 postpartum in appropriate groups in order to allow recovery of cows from parturition, to avoid administration of rbSt during the typical early postpartum lactation fluctuations of both milk yield and milk components, and to identify cows which the herdsman judged to be candidates to complete at least 130 d of lactation. Dose changes of rbSt take place at d 61 postpartum. Day 60 is generally an acceptable standard time at which breeding of dairy cattle should begin and is post-peak of lactation and near the postpartum time of return to positive energy balance (EB). This allows comparisons of reproductive performance in cows given rbSt prior to and starting at d 60 postpartum.

Replacement of cows removed from study occurs prior to commencement of injections (i.e., prior to d 14 postpartum). Replacement is with the next available cow. Cows lost after d 14 postpartum are not replaced. Unequal experimental groups may result due to cows being removed between 14 and 90 d postpartum.

Intramuscular Injections: The rbSt is produced in house. Bottles of lyophilized rbSt are stored at 4° C. Bottles of rbSt are solubilized on the day of use with 21 ml sterile distilled water. Unused solubilized rbSt is stored in a refrigerator and is used on the next day only. Final concentration is 8.6 mg rbSt/ml. Cows receiving a 14 mg rbSt dose are injected with 1.6 ml (13.8 mg) and cows receiving a 5 mg dose are injected with 0.6 ml (5.2 mg). Injections are administered in the semitendinosus muscle once daily using a 3 ml disposable syringe with a 23 g, 1.9 cm needle. Injections are performed in freestalls prior to a.m. milking (0500–0545) by the herdsmen. Cows to be injected are marked by crayon on the hindlimb with a single (5 mg dose) or double (14 mg dose) slash.

Data Collection: Cows are milked at a.m. (0600–1330) and p.m. (1800–0130) according to the routine schedule of the herd. In addition, cows are fed to production, regardless of treatment group. Cows are group fed a standard total mixed ration. As production declines, some animals are moved to an adjacent pen where diet ingredient amounts are altered to reduce protein and energy to meet production needs. In general, cows are moved from the high production pen when daily milk is below 36 kg or after 100 days in milk. Milk weights are recorded electronically (Bou-Matic milk flow meters) at each milking. Milk fat is determined every 2 weeks by an independent laboratory (G. Wise; Scotts, Mich.). Visual appraisal of body condition (1=very thin, 5=very fat; according to the method of E. E. Wildman, G. M. Jones, P. E. Wagner, R. L. Boman, H. F. Troutt, T. N. Lesch (1982), "A Dairy Cow Body Condition Scoring System and its Relationship to Selected Production Characteristics", J. Dairy Sci., 1981, 64:495) is performed every two weeks on a given day of the week by consensus of the herdsmen for each cow on experiment. In addition, the herd maintained accurate breeding records such as dates of estrus, artificial insemination (AI) and confirmed pregnancies. All cows are examined at two-week intervals starting approximately 40 d postpartum by the herd veterinarian and cows are pregnancy checked 40 to 45 d after AI. Herd policy is to begin AI after 40 d postpartum. In response to veterinary recommendations and consistent with usual management of the herd, cows are treated for diagnosed maladies. For example, cows with mastitis or metritis receive appropriate antibiotics and instances of cystic ovaries or anestrus are treated with exogenous gonadotropins or prostaglandin $F_{2\alpha}$. On herds with a good reproductive program, greater than 50% of cows should be confirmed pregnant by d 130 postpartum (J. R. Chenault, "Effect of Fertirelin Acetate or Buserelin on Conception Rate at First or Second Insemination in Lactating Dairy Cows", J. Dairy Sci., 73:633 (1990)); therefore, the trial ends at d 130. Statistical analyses are performed on FCM, lactation curve (slope to peak, time to peak, amplitude, slope post peak), days to first estrus, days to first AI, days open, inter-estrus intervals, first service conception rate, pregnancy rate, and services per conception. Numbers of cows removed from study and reasons for removal are monitored for any relationship to treatment.

All reproductive and health related variables are calculated based on events which occur during the trial duration of 130 d postpartum. Reproductive variables are calculated based on days open, conception rate, first service conception rate, second service conception rate, pregnancy rate, and services per conception.

Statistical Analyses: A randomized complete block design are utilized. The five treatments are ordered randomly in 42 blocks on an assignment sheet, and animals calving sequentially are assigned between d 11 to 14 postpartum to treatments.

For milk yield, the primary response variable of interest is average daily 3.5% FCM from start of injection (d 14 postpartum) through d 130 postpartum. Average daily FCM also is examined from d 14 to d 60 to examine effect of rbSt dose (5 mg/d versus 14 mg/d versus control) during early lactation. For lactation curve analyses, slope to peak and slope post peak are determined for each cow by regression analysis. Peak is the maximum FCM observed during d 14 through 130 of lactation. If peak FCM occurs on a day of lactation less than 16 or greater than 128 d, the slope is regarded as missing. There are no instances of this occurring.

The 3.5% FCM yield adjustment are based on H. F. Tyrrell, J. T. Reid, "Prediction of the Energy Value of Cow's Milk", J. Dairy Sci. 48:1215 (1965), and the specific equation of G. E. Stoddard, "How Fat-Corrected Milk Originated", Hoard's Dairyman, March 10, 1980, p. 319 (3.5% FCM=0.432 kg milk+16.23 kg fat.). Milk yield from d 1 to 14 of lactation is used as a covariate (S. R. Lowry, F. G. Owen, "Potential of Milk Yield in Short Segments of Early Lactation as Covariates in Feeding Experiments", J. Dairy Sci. 64:533 (1981)), in the analysis. Milk yield between d 11 to 14 has a correlation to 305 d yield of 0.4 (id). This model without covariate also is used to analyze slope to peak, days to peak, amplitude of peak, slope post peak, time to first estrus/service, days open, conception rate and pregnancy rate. Body condition is analyzed with and without a covariate. Analyses with covariate also are tested for heterogeneity of slopes among treatment groups.

Chi square analysis are used to test for treatment differences in occurrence of cystic ovaries, anestrus, mastitis and metritis.

Milk Yield: Referring to Table 1, cattle produce quantities of FCM during the first 13 d postpartum that does not differ (P>0.30) among experimental groups, averaging between 29.7 and 31.0 kg/d (Table 1). During 14 to 60 d postpartum, cows in groups C and OH have not received rbSt, and, thus, data are pooled from these two groups of cows to compare with cows that receive 5 mg of rbSt/d (L and LH) and with high (H) rbSt dosed cows during this interval. Cattle given 5 mg rbSt daily produces 1.2 kg more (39.2 kg P=0.02) FCM per day and H cows produces 1.3 kg more (39.3 kg P<0.05) FCM daily than non-injected (38.0 kg) cattle between 14 and 60 d postpartum (Table 1). However, FCM does not differ between L and H cows (P=0.88). These results agree with previous work by A. L. Richard, et al., "Responses of Dairy Cows to Exogenous Bovine Growth Hormone Administered During Early Lactation", J. Dairy Sci., 68:2385 (1985), that exogenous bSt is effective at stimulating milk yields during early lactation, even when commencement of treatment begins on 14 d postpartum. However, rinse results do not support an rbSt dose range in FCM response during 14 to 60 d postpartum similar to that during 70 to 305 d postpartum, see E. P. Stanisiewski, et at., "Production Performance of Dairy Cattle Administered Recombinantly Derived Bovine Somatotropin Daily: A Dose Range Study", J. Dairy Sci. (In Press), since, surprisingly, FCM is not different between cows receiving 5 or 14 mg of rbSt per day.

Control cows produce 33.3 kg FCM/d between 61 and 130 d postpartum, which is less (P<0.002) than production by each of the groups receiving rbSt (Table 1). However, the lowest response compared with controls is in group L (36.0 kg FCM/d; P<0.002; Table 1) while the highest FCM responses are seen in groups OH (37.4 kg/d, P<0.0001) and LH (37.7 kg/d, P<0.0001). Milk produced by H-dosed cows (36.2 kg/d) is suggestive of being different (P<0.10) from cows of the LH group (Table 1). In addition, cows given rbSt in a LH pattern produce 1.7 kg more (P=0.04) daily FCM during d 61 to 130 than cattle on L dosing. These data show that cows exhibit an incremental increase in FCM in response to 5 and 14 mg of rbSt during 60 to 130 d which is absent during 14 to 60 d postpartum.

Average FCM production during the trial duration (d 14 to 130 postpartum) is 2.2 to 3.2 kg/d greater (P<0.005) in rbSt dosed cows compared with controls (35.1 kg FCM/d; Table 1). Mean FCM of experimental groups receiving rbSt during the trial (d 14 to d 130) are not significantly different (P=0.15 to P=0.82) although lowest numerical response compared with controls are in L group cows (37.3 kg/d) and highest numerical response are in LH group cows (38.3 kg/d; Table 1).

Milk yield on day of peak production average 46.9 kg in controls which are not significantly different (P>0.10) from other treatment groups although cattle of the H rbSt group peak 2.3 kg higher (P=0.14) and cattle of the LH group peak 2.4 kg higher (P=0.13) than controls (Table 2). Peak yield of controls occurs 44.1 d postpartum while OH cattle peak 19.8 d later (P=0.005; Table 2). Administration of rbSt to OH cattle begin 60 d postpartum which are after the inherent (approximately 44 d postpartum) peak of controls. Initiation of rbSt dosing pre-peak appears to have a minimal effect on changing the temporal occurrence of peak since cows of L, LH and H groups peaked on d 55.9, 56.0 and 51.4 which are not different (P>0.10) from controls (Table 2).

Overall, pre-peak FCM slopes are similar among treatment groups (Table 2), however, cattle in groups L (slope=0.22) and H (slope=0.59) represent extremes of the range which differ from each other at P=0.06. Post-peak FCM declined least rapidly in groups OH and are most rapid in group H (slopes=−0.06 and −0.25, P=0.08; Table 2). During 14 to 60 d postpartum FCM responses are similar in cattle given 5 (L and LH) or 14 (H) mg of rbSt/d.

Reproduction: Average days open during 130 d of trial are unaffected (P=0.91) by rbSt administration and ranged from 78.4 to 85.0 d (Tables 3(a) and 3(b)). In addition, services per conception are not different (P=0.96) among treatments averaging 1.39 to 1.56 (Tables 3(a) and 3(b)). However, cattle of group L have an improved (P=0.04) pregnancy rate (80.0%) when compared with cows of group H (57.2%; Tables 4(a)–(c)). Pregnancy rate of control cows (70.0%) are not significantly different (P=0.24 to P=0.48) from any of the other groups (Tables 4(a)–(c)). Cattle of both groups LH (62.3%) and OH (62.3%) tend (P=0.10) to have reduced pregnancy Similarly, conception rates reflected pregnancy rate patterns; cows in group L have the highest rate (82.2%) which is better (P=0.05) than that of H cows (60.3%, Table 5). Cows in group L also have a numerically improved conception rate when compared with either LH (63.9%, P=0.09) or OH (65.8%, P=0.14) cows (Tables 5(a) and 5(b)). First service conception rates are not different (P=0.95) for C (44.8%) and OH (45.6%) cattle (Tables 5(a) and 5(b)). However, among cattle which are dosed with rbSt both prior to and after d 60, L group cattle have a first service conception rate of 57.8% compared with rates of 34.3% (P=0.05) for group H and 38.2% (P=0.10) for LH cows (Tables 5(a)–(b)). First estrus is observed in cattle of group H (57.1 d) approximately 16 to 13 d later (P<0.05) than cattle of group L (41.1 d) and LH (44.0 d, Tables 5(a) and 5(b)). In addition, L-dosed cattle have first observed estrus 9 d sooner (P=0.17) than controls. Furthermore, LH cows return to estrus about 11 d sooner (P=0.10) than OH cows. These data show that low dosing of rbSt (L and LH) during the early postpartum period may reduce days to first postpartum estrus.

Treatment group differences in days to first estrus are not reflected to the same extent in days to first service although cows of group H are serviced about 7 d later than either L (P=0.14) or LH (P=0.17) cows (Table 5). This lack of difference for days to first service among cows of the 5 groups are likely due to the fact that herd management deemed breeding to start after 40 d postpartum, thus estrus detected earlier are of little advantage under this management program in terms of affecting days to first service. However, once estrus cycles are initiated postpartum, dairy cows appear to estrus cycle regularly; and, earlier estrus cycle establishment provide multiple estrus cycles prior to initiation of breeding which result in a positive effect on conception rates (see, W. R. Buffer and R. D. Smith, "Interrelationships Between Energy Balance and Postpartum Reproductive Function in Dairy Cattle", J. Dairy Sci., 72:767 (1989) and C. R. Staples, et al., "Relationship Between Ovarian Activity and Energy Status During the Early Postpartum Period of High Producing Dairy Cows", J. Dairy Sci., 73:938 (1990)).

TABLE 1

| | | Avg. Postpartum kg 3.5% FCM/Day | | | |
|---|---|---|---|---|---|
| Treatment | n | 1 through 13d | 14 through 60 d | 61 through 130d | Total (14 through 130d) |
| C | 39 | 31.0 | 37.9$^a$– | 33.3$^{ad}$ | 35.1$^d$ |
| OH | 40 | 29.7 | 38.1$^{ab}$–38.0$^d$ | 37.4$^{bce}$ | 37.6$^e$ |
| L | 40 | 29.9 | 39.1$^b$– | 36.0$^{bc}$ | 37.3$^e$ |
| LH | 40 | 29.8 | 39.2$^b$–39.2$^e$ | 37.7$^{ee}$ | 38.3$^e$ |
| H | 40 | 30.6 | 39.3$^b$–39.3$^e$ | 36.2$^{be}$ | 37.4$^e$ |

TABLE 2

| | Milk Peaks and Slope Characteristics | | | |
|---|---|---|---|---|
| Treatment | Peak FCM (kg/d)$^f$ | Day of Peak | Pre-Peak Slope (Kg/d)$^g$ | Post-Peak Slope (kg/d)$^h$ |
| C | 46.9 | 44.1$^{ad}$ | .33$^{ab}$ | −.12$^{ab}$ |
| OH | 48.3 | 63.9$^{be}$ | .42$^{ab}$ | −.06$^a$ |
| L | 47.2 | 55.9$^{bcde}$ | .22$^a$ | −.10$^{ab}$ |
| LH | 49.3 | 56.0$^{bcde}$ | .35$^{ab}$ | −.08$^{ab}$ |
| H | 49.2 | 51.4$^{acde}$ | .59$^b$ | −.25$^b$ |

$^{abc}$Values in a column with different superscripts differ (P ≤ .10) from each other.
$^{de}$Values in a column with different superscripts differ (P ≤ .05) from each other.
$^f$Peak is defined as maximum daily FCM per cow between 14 and 130 d postpartum. Day of peak is the postpartum day on which peak occurred.
$^g$Day 14 to day of peak.
$^h$Day of peak to d 130 postpartum.
$^i$Mean square error.

TABLE 3(a)

Least Squares Means and Levels of Significance (P Values) for all Treatment Group Contrasts for Days Open and Services per Conception
Days Open

| Treatment | C | H | L | LH | OH | |
|---|---|---|---|---|---|---|
| Means | 85.0 | 79.9 | 78.4 | 83.1 | 81.1 | |
| P-Values: | — | .53 | .37 | .81 | .62 | C |

TABLE 3(a)-continued

Least Squares Means and Levels of Significance (P Values) for all Treatment Group Contrasts for Days Open and Services per Conception Days Open

| Treatment | C | H | L | LH | OH |
|---|---|---|---|---|---|
| | | — | .84 | .70 | .89 H |
| | | | — | .53 | .72 L |
| | Overall | | | — | .81 LH |
| | treatment | | | | |
| | Effect: P = .91 | | | | — OH |

TABLE 3(b)

Services per Conception

| C | H | L | LH | OH |
|---|---|---|---|---|
| 1.56 | 1.39 | 1.43 | 1.45 | 1.42 |
| — | .48 | .55 | .63 | .55 |
| | — | .86 | .81 | .91 |
| | | — | .93 | .97 |
| Overall | | | — | .91 |
| treatment | | | | |
| Effect: | | | | |
| P = .96 | | | | |

TABLE 4(a)

Least Squares Means and Levels of Significance (P Values) for all Treatment Group Contrasts for Pregnancy Rate, Conception Rate, and First Service Conception Rate Pregnancy Rate (%)

| Treatment | C | H | L | LH | OH | |
|---|---|---|---|---|---|---|
| Mean: | 70.0 | 57.2 | 80.0 | 62.3 | 62.3 | |
| P-values | — | .24 | .36 | .48 | .48 | C |
| | | — | .04 | .64 | .64 | H |
| | | | — | .10 | .10 | L |
| | Overall | | | — | 1.00 | LH |
| | treatment | | | | | |
| | Effect: | | | | — | OH |
| | P = .25 | | | | | |

TABLE 4(b)

Conception Rate (%)

| C | H | L | LH | OH |
|---|---|---|---|---|
| 71.5 | 60.3 | 82.2 | 63.9 | 65.8 |
| — | .31 | .33 | .49 | .61 |
| | — | .05 | .74 | .62 |
| | | — | .09 | .14 |
| Overall | | | — | .86 |
| treatment | | | | |
| Effect: | | | | — |
| P = .31 | | | | |

TABLE 4(c)

First Service Conception Rate (%)

| Treatment | C | H | L | LH | OH | |
|---|---|---|---|---|---|---|
| Mean: | 44.8 | 34.3 | 57.8 | 38.2 | 45.6 | |
| P-Values: | — | .38 | .28 | .58 | .95 | C |
| | | — | .05 | .75 | .36 | H |
| | | | — | .10 | .32 | L |
| | Overall | | | — | .54 | LH |

TABLE 4(c)-continued

First Service Conception Rate (%)

| Treatment | C | H | L | LH | OH |
|---|---|---|---|---|---|
| Treatment | | | | | |
| Effect: | | | | | — OH |
| P = 25 | | | | | |

TABLE 5(a)

Least Squares Means and Levels of Significance (P Values) for all Treatment Group Contrasts for Days to First Estrus, and Days to First Service Days to First Estrus

| Treatment | C | H | L | LH | OH | |
|---|---|---|---|---|---|---|
| Mean: | 50.1 | 57.1 | 41.1 | 44.0 | 55.2 | |
| P-Values: | — | .29 | .17 | .36 | .45 | C |
| | | — | .02 | .05 | .77 | H |
| | | | — | .66 | .04 | L |
| | Overall | | | — | .10 | LH |
| | Treatment | | | | | |
| | Effect: | | | | — | OH |
| | P = .08 | | | | | |

TABLE 5(b)

Days to First Service

| C | H | L | LH | OH |
|---|---|---|---|---|
| 71.8 | 76.9 | 69.6 | 70.2 | 75.8 |
| — | .31 | .65 | .73 | .43 |
| | — | .14 | .17 | .83 |
| | | — | .91 | .21 |
| Overall | | | — | .26 |
| Treatment | | | | |
| Effect: | | | | — |
| P = .47 | | | | |

I claim:

1. A method for increasing fertility in cattle, comprising administering an effective amount of somatotropin to a cow beginning in the early postpartum period.

2. The method of claim 1 wherein the amount of somatotropin is less than 14 mg/day.

3. The method of claim 2 wherein the administration commences no sooner than 5 days postpartum.

4. The method of claim 3 wherein the administration continues until pregnancy is established or until about 100 days postpartum, whichever occurs first.

5. The inethod of claim 4 wherein the amount of somatotropin is 5 mg/day.

6. The method of claim 4 wherein the administration commences at about 14 days postpartum.

7. The method of claim 1 wherein administration is by parenteral means.

8. The method of claim 7 wherein administration is by subcutaneous injection.

9. A method for increasing the yield of fat corrected milk in cattle, comprising administering an effective amount of somatotropin to a cow beginning in the early postpartum period, wherein the amount of somatotropin is less than 14 mg/day and administration continues until pregnancy is established or until about 60 days postpartum, whichever occurs first.

10. The, method of claim 9 wherein administration commences no sooner than 5 days postpartum.

11. The method of claim 9 wherein administration is by subcutaneous injection.

12. A method of enhancing both reproductive efficiency and fat corrected milk yield in cows which comprises:
 (a) administering an effective amount of somatotropin to a cow during a first treatment period, the first treatment period beginning at day zero (0) of early postpartum and continuing until either pregnancy is established or until about 100 days postpartum, whichever occurs first, and
 (b) administering an amount of somatotropin to the cow, said amount effective to cause or maintain an increase in fat corrected milk, during a second treatment period, the second treatment period to commence following cessation of the first treatment period.

13. The method of claim 12 wherein administration of somatotropin during the first treatment period is less than 14 mg/day and during the second treatment period is about 5 to 50 mg/day.

14. The method of claim 13 wherein administration of somatotropin during the first treatment period commences at about day 14 in an amount of 5 mg/day, and administration during the second treatment period commences one day following cessation of the first treatment period in an amount of about 14 mg/day.

* * * * *